United States Patent
Cheng et al.

(10) Patent No.: US 12,329,804 B2
(45) Date of Patent: *Jun. 17, 2025

(54) MODIFIED CHEMOKINE PEPTIDE AND USE THEREOF

(71) Applicant: Rise Biopharmaceuticals Inc., Beijing (CN)

(72) Inventors: Jya-Wei Cheng, Tainan (TW); Hsi-Tsung Cheng, Tainan (TW); Hui-Yuan Yu, Tainan (TW); Su-Ya Hsu, Tainan (TW)

(73) Assignee: RISE BIOPHARMACEUTICALS INC., Beijing (CN)

( * ) Notice: Subject to any disclaimer, the term of this patent is extended or adjusted under 35 U.S.C. 154(b) by 1220 days.

This patent is subject to a terminal disclaimer.

(21) Appl. No.: 17/006,512

(22) Filed: Aug. 28, 2020

(65) Prior Publication Data

US 2021/0046158 A1 Feb. 18, 2021

Related U.S. Application Data

(63) Continuation-in-part of application No. 15/569,033, filed as application No. PCT/CN2015/008725 on Jun. 3, 2015, now abandoned.

(60) Provisional application No. 62/959,553, filed on Jan. 10, 2020, provisional application No. 62/927,829, filed on Oct. 30, 2019.

(51) Int. Cl.
A61K 38/19 (2006.01)
A61P 35/00 (2006.01)

(52) U.S. Cl.
CPC ............ *A61K 38/195* (2013.01); *A61P 35/00* (2018.01)

(58) Field of Classification Search
None
See application file for complete search history.

(56) References Cited

U.S. PATENT DOCUMENTS 5,595,756 A    1/1997   Bally et al.

FOREIGN PATENT DOCUMENTS

| CN | 101200502 A | 6/2008 |
|----|-------------|--------|
| CN | 102596227 A | 7/2012 |
| EP | 0616615 A1  | 9/1994 |
| EP | 0616615 B1  | 8/1998 |
| WO | WO-9311159 A1 | 6/1993 |

OTHER PUBLICATIONS

Heppner et al. (Cancer Metastasis Review 2:5-23; 1983) (Year: 1983).*
Hait (Nature Reviews/Drug Discovery, 2010, 9, pp. 253-254) (Year: 2010).*
Gravanis et al. (Chin Clin Oncol, 2014, 3(2):22) (Year: 2014).*
Beans (PNAS 2018; 115(50): 12539-12543) (Year: 2018).*
Bowie, James U. et al., "Deciphering the Message in Protein Sequences: Tolerance to Amino Acid Substitutions", Science, vol. 247, Mar. 16, 1990, pp. 1306-1310.
Burgess et al., "Possible dissociation of the heparin-binding and mitogenic activities of heparin-binding (acidic fibroblast) growth factor-1 from its receptor-binding activities by site-directed mutagenesis of a single lysine residue", Journal of Cell Biology, vol. 111, Issue 5, Nov. 1, 1990, pp. 2129-2138.
Jain, RK, "Barriers to Drug Delivery in Solid Tumors," Scientific American, vol. 271, Issue 1, Jul. 1994, pp. 58-65.
Gura, T, "Systems for identifying new drugs are often faulty", Science, vol. 278(5340), Nov. 7, 1997, pp. 1041-1042.
Lazar et al., "Transforming Growth Factor a: Mutation of Aspartic Acid 47 and Leucine 48 Results in Difference biological Activies". Molecular and Cellular Biology, vol. 8, Issue No. 3, Mar. 1998, pp. 1247-1252.
Bork, Peer, "Powers and Pitfalls in Sequence Anayalsis the 70& Hurdle", Genome Research, vol. 10, Issue No. 4, 2000, pp. 398-400, 2000.
Sporn, Michael et al, "Chemoprevention of Cancer," Carcinogenesis, vol. 21, Issue No. 3, Mar. 2000, pp. 525-530.
Auerbach, Robert et al. Angiogenesis assays: Problems and pitfalls:, Cancer and Metastasis Reviews, Issue 19, Jun. 1, 2000, pp. 167-172.
Le, Y.Y. et al., "Chemokines and Chemokine Receptors: their Maniold Roles in Homeostasis and Disease", Cellular & Molecular Immunology, Apr. 30, 2004, vol. 1, Issue No. 2., pp. 95-101.

* cited by examiner

Primary Examiner — Brian Gangle
Assistant Examiner — Andrea K McCollum
(74) Attorney, Agent, or Firm — MUNCY, GEISSLER, OLDS & LOWE, P.C.

(57) ABSTRACT

The present invention provides a novel modified chemokine peptide. Additionally, the novel modified chemokine peptide can be used to treat cancer and inhibit tumor growth more effectively.

4 Claims, 10 Drawing Sheets

Specification includes a Sequence Listing.

MODIFIED CHEMOKINE PEPTIDE AND USE THEREOF

CROSS-REFERENCE TO RELATED APPLICATIONS

This application is a Continuation-in-Part of U.S. application Ser. No. 15/569,033, entitled "MODIFIED CHEMOKINE PEPTIDE", filed on Oct. 24, 2017, which claims the benefit of this is a National Phase Application filed under 35 U.S.C. 371 as a national stage of PCT/CN2015/080725, filed Jun. 3, 2015, the content of which is hereby incorporated by reference in its entirety.

This application claims also partial priority in U.S. Provisional Patent Application No. 62/927,829, filed Oct. 30, 2019, and partial priority in U.S. Provisional Patent Application No. 62/959,553, filed Jan. 10, 2020, which is incorporated by reference in its entirety herein.

STATEMENT REGARDING THE SEQUENCE LISTING

The content of the electronic sequence listing (2024-12-23-Sequence-Listing.txt; Size: 2,228 bytes; and Date of Creation: Nov. 21, 2024) is herein incorporated by reference in its entirety.

FIELD OF THE INVENTION

The present invention relates to a novel modified chemokine peptide capable of being a therapeutic antagonist. In particular, the present invention relates to a modified chemokine for treating cancer and inhibiting tumor growth.

BACKGROUND OF THE INVENTION

Chemokines are a group of inducible, secretory, structurally and related small molecules (approximately 8 to 14 kD). Chemokine is divided into four subfamilies, such as CXC, CC, CX3C and C. Chemokines are also grouped into two main functional subfamilies: "homeostatic chemokines" and "inflammatory chemokines".

Chemokine usually has three β-sheets in its structure, and has a α-helix at C terminal and more than 2 conserved cysteines at N-terminus. Chemokines have been categorized into four subfamilies (CXC, CC, CX3C and XC) based on the sequence containing the first two cysteines (Cys) at N-terminus. Among the four types, CXC and CC are the two major subfamilies while XC and CX3C are minor subfamilys. Chemokine biological activities are mediated by chemokine receptors. Chemokine receptors are G protein-coupled seven-transmembrane signaling receptors. The family of chemokine receptors consists of 18 members divided into several classes according to their ligands, chemokines, which are classified based on the spatial arrangement of cysteine residues in their amino terminus: 10 CC chemokine receptors (CCR1-10), 6 CXC chemokine receptors (CXCR1-6), 1 CX3C chemokine receptor (CX3CR1), and 1 C chemokine receptor (XCR1). Further, some chemokine receptors, such as CXCR2, CCR1, CCR2, CCR3 or CCR5, have multiple ligands, while others including CXCR4, CXCR5, CXCR6, CCR8 or CCR9 are specific receptors for one single ligand.

For instance, ELR-CXC chemokine with glutamate (E)-leucine (L)-Arginine (R) characteristic sequence (ELR characteristic sequence) is referred to a protein having the amino acid sequence of ELR-CXC characteristic at N-terminus, and X would be the amino acid having polarity with or without charge. ELR-CXC chemokine always means CXCL1, CXCL2, CXCL3, CXCL5, CXCL6, CXCL7, CXCL8. Their receptors are CXCR1 and CXCR2, and they mainly target to neutrophils. ELR-CXC chemokine can promote the accumulation and activation of neutrophils.

Additionally, ELR-CXC chemokine is associated with angiogenesis accompanied upon tumor development, and its inductive mechanism is the activation generated by conjugating this type of chemokine, especially referring to CXCL8, with CXCR1 and CXCR2 on the endothelial cells (ECs). At present, it is proved that many different types of tumors are able to secret ELR-CXC chemokines, and the tumors overexpressing these chemokines would be associated with poor prognosis.

In other word, it is a practicable strategy that the prosurvival, proliferation, metastasis signals following CXCR1 or/and CXCR2 activation could be inhibited via administering antagonist of CXCR1 or CXCR2 competitive to ELR-CXC chemokine. Thus, blockade of the chemokine receptor CXCR1 or/and CXCR2 would be indicative of an increased well treatment. Therefore, it is a very urgent and important issue that how to develop antagonists for these chemokine receptors or/and chemokine-analogous proteins quickly, and reduce the probability of clinical failure for treating various disease (e.g., cancer).

It is therefore attempted by the applicant to deal with the above situation encountered in the prior art.

SUMMARY OF THE INVENTION

Cancer is the most popular disease cause of death in developed countries. If cancer is diagnosed at an early stage, it is more likely to be treated successfully. Although there has been considerable progress in the diagnosis and treatment of cancer, these drugs are either causing serious side effects or ineffective. Therefore, a novel method or a novel composition for treating cancer or preventing cancer is needed.

In order to solve the above-mentioned problems, according to one embodiment of the present invention, there is provided a novel modified chemokine for inhibiting tumor growth and treating cancer.

The present invention also provides a pharmaceutical composition, comprising the modified chemokine peptide of the present invention and a pharmaceutically acceptable excipient.

In one embodiment, the modified chemokine peptide is used for treating cancer or inhibiting tumor growth.

The present invention further provides a pharmaceutical composition for treating cancer or inhibiting tumor growth, comprising a therapeutically effective amount of a modified chemokine peptide of the present invention and a pharmaceutically acceptable excipient.

In one embodiment, the cancer comprises prostate cancer, breast cancer, uterine cancer, leukemia, ovarian cancer, endometrial cancer, cervical cancer, colorectal cancer, testicular cancer, lymphoma, rhabdomyosarcoma, neuroblastoma, pancreatic cancer, lung cancer, brain tumor, skin cancer, stomach cancer, oral cancer, liver cancer, laryngeal cancer, gallbladder cancer, thyroid cancer, liver cancer, kidney cancer, or nasopharyngeal carcinoma.

Detailed description of the invention is given in the following embodiments with reference to the accompanying drawings.

DETAILED DESCRIPTION OF THE INVENTION

Figure 1:
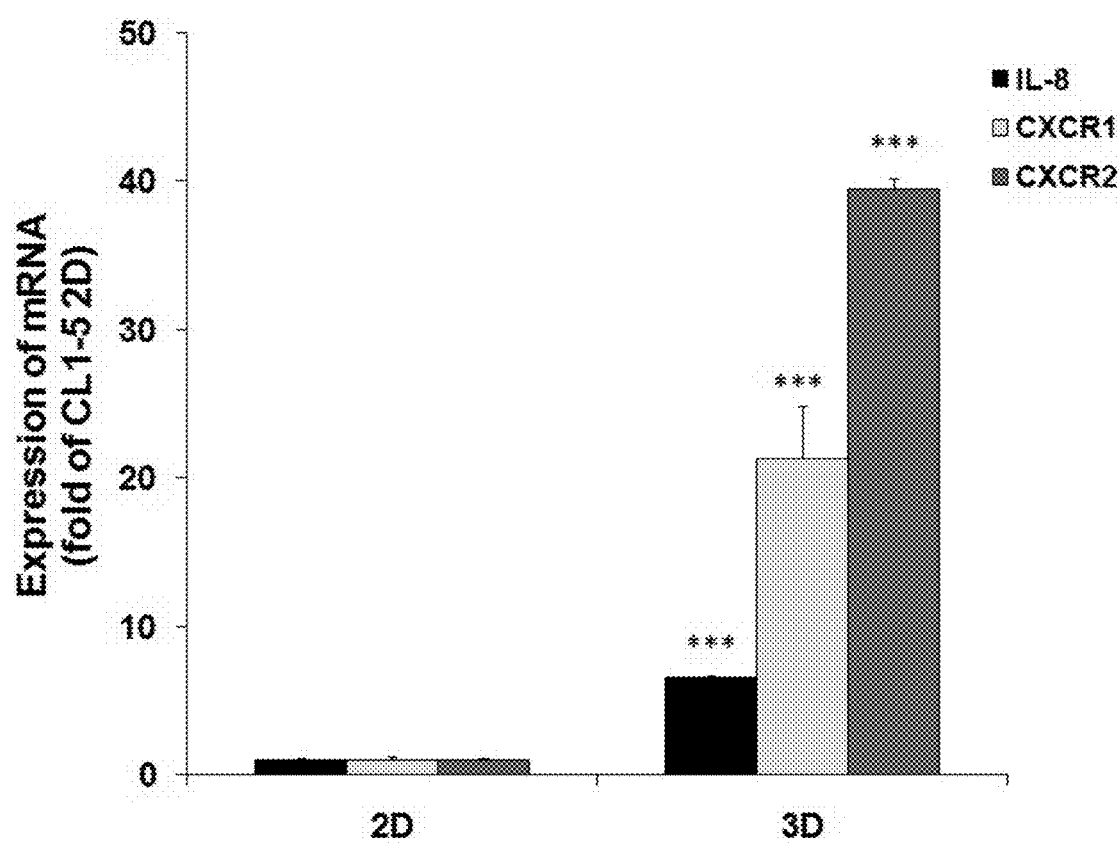
FIG. 1 illustrates that CL1-5 NSCLC cells show higher IL-8 and IL8R gene expression in 3D (suspended) condition compared to 2D (attached) cell culture.

The present invention provides a novel chemokine. Optionally, in an exemplary embodiment of the present invention, the novel modified chemokines of the present invention include, but are not limited to, SEQ ID NO: 1 (RP72).

Sequences of SEQ ID NO: 1 (RP72) which can be employed in accordance with the invention are shown hereinbelow:

```
SEQ ID NO: 1:
GSKELRCQCIRSYSKPFHPKFIKELRVIPASQFCANTEIIVKLSDGRELC

LDPKENWVQRVVEKFLKRAENS
```

The modified chemokine of the present invention, an analogs and fragments thereof can treat diseases associated with angiogenesis. The angiogenesis associated diseases include, but are not limited to, inflammatory disorders, disorders associated with inappropriate or inopportune invasion of vessels such as cell proliferation disorder/disease, such as neoplasm and cancer associated disorders (e.g., prostate cancer, breast cancer, uterine cancer, leukemia, ovarian cancer, endometrial cancer, cervical cancer, colorectal cancer, testicular cancer, lymphoma, rhabdomyosarcoma, neuroblastoma, pancreatic cancer, lung cancer, brain tumor, skin cancer, stomach cancer, oral cancer, liver cancer, laryngeal cancer, gallbladder cancer, thyroid cancer, liver cancer, kidney cancer, or nasopharyngeal carcinoma).

In another embodiment, the cancer is selected from pleural-related cancer, gastrointestinal tract-related cancer, abdominal-related cancer, and endocrine-related cancer. Additionally, the pleural-related cancer is selected from the group consisting of lung cancer, large cell lung cancer, squamous cell lung cancer, small cell lung cancer and non-small cell cancer. The gastrointestinal tract-related cancer is selected from pancreatic cancer, hepatic cancer, gastric cancer, colorectal cancer, and tongue cancer. The abdominal-related cancer is selected from bladder cancer, and cervical cancer. The endocrine-related cancer is selected from prostate cancer, breast cancer, and ovarian cancer.

The novel modified chemokine of the present invention can be administered orally, buccally, parenterally, by inhalation spray, rectally, intradermally, transdermally, or topically in dosage unit formulations containing conventional nontoxic pharmaceutically acceptable carriers, adjuvants, and vehicles as desired.

The novel modified chemokine of the present invention can be administered in a single dose, in multiple doses throughout a 24-hour period, or by continuous infusion. When administered by continuous infusion, the compounds can be supplied by methods well known in the art, such as, but not limited to, intravenous gravity drip, intravenous infusion pump, implantable infusion pump, or any topical routes. Length of treatment will vary depending on many factors, for example, the duration and severity of the angiogenesis condition. Treatment of the subject with the modified chemokine of the present invention alone or in combination with other agents may last until the angiogenesis disappears, or treatment will continue for the life of the subject.

In another embodiment, the present invention provides a pharmaceutical composition for treating cancer and inhibiting tumor. The pharmaceutical composition comprises an effective amount of a modified chemokine of the present invention or analogs thereof and a pharmaceutically acceptable carrier. The pharmaceutically acceptable carrier could include solvent, dispersants, coating, antibacterial/antifungal agents, isotonicity agents, controlled release agents and/or analogues thereof.

Additional specific embodiments of the present invention include, but are not limited to the following:

Example 1

Cell Line

CL1-5, a cell subline from human lung adenocarcinoma CL1, was maintained in RPMI 1640 medium supplemented with 10% fetal bovine serum, 1% penicillin-streptomycin, and 1% L-Glutamine in a humidified cell culture incubator at 37° C. in 5% $CO_2$. Also, CL1-5 was transfected virus with human IL-8 knockdown plasmid to obtain IL-8 knock down CL1-5 cell line.

Lewis lung carcinoma (LL/2) is a cell line established from the lung of a C57BL mouse bearing a tumor resulting from an implantation of primary Lewis lung carcinoma. This lung cancer cell lines grow in Dulbecco's Modified Eagle's Medium with 10% FBS, 1% penicillin-streptomycin, and 1% L-Glutamine in a humidified cell culture incubator at 37° C. in 5% $CO_2$.

Human pancreatic cancer (PDAC) cell lines, BxPC3, are maintained in RPMI 1640 media with 10% FBS, 1% penicillin-streptomycin, 100 mM L-glutamine, 100 nM HEPES, 10 nM Sodium pyruvate and 25 nM Glucose.

Human umbilical vein endothelial cells (HUVEC) grows in Medium 199 with 15 μg/mL Endothelial cell growth supplement from bovine neural tissue, 10% FBS, 1% penicillin-streptomycin, and 1% L-Glutaminein a humidified cell culture incubator at 37° C. in 5% $CO_2$.

Example 2

Expression Level of CXCR1/2 and CXCL8 Genes in Tumor Cells

Total RNA from cells was isolated by RNA Extraction Reagent (REzol™ C & T, Protech Technology Enterprise Co., Taiwan) and quantified by spectrophotometer (Nanodrop 1000, Thermo Scientific). Single-stranded cDNA was synthesized using PrimeScript RT Reagent Kit (Perfect Real Time) (RR037A, TAKARA Bio, Japan) according to the user manuals.

All real-time PCR reactions were performed with 2× qPCRBIO ProbeMix Hi-ROX reagent (PCR Biosystems, UK) and UPL probe system (IL-8, CXCR1, CXCR2) by an StepOnePlus™ Real-Time PCR System (Applied Biosystems™). 18 s was used as an internal loading control. Sequences of the primers included:

```
                                       (SEQ ID NO: 2)
5'-gagcactccataaggcacaaa-3' (forward primer for CXCL8)
and (SEQ ID NO: 3)
5'-atggttccttccggtggt-3' (reverse primer for

CXCL8);

(SEQ ID NO: 4)
5'-gaccaacatcgcagacacat-3' (forward primer for

CXCR1)
and (SEQ ID NO: 5)
5'-tgcttgtctcgttccacttg-3' (reverse primer for

CXCR1);

(SEQ ID NO: 6)
5'-ggctaagcaaaatgtgatatgtacc-3' (forward primer for CXCR2)
and (SEQ ID NO: 7)
5'-caaggttcgtccgtgttgta-3' (reverse primer for

CXCR2).
```

The gene expression was calculated by the following formula: gene expression=$2^{-\Delta\Delta Ct}$.

Please refer to FIG. 1, it is much more difference of RP72 effects between 2D (attached) and 3D (suspended) is associated with IL-8. The Q-PCR results with 2D and 3D-cultured CL1-5 (FIG. 1) indeed show significantly higher IL-8 and IL-8R (CXCR1/2) mRNA expression in 3D-cultured cells.

Example 3

Figure 2A:
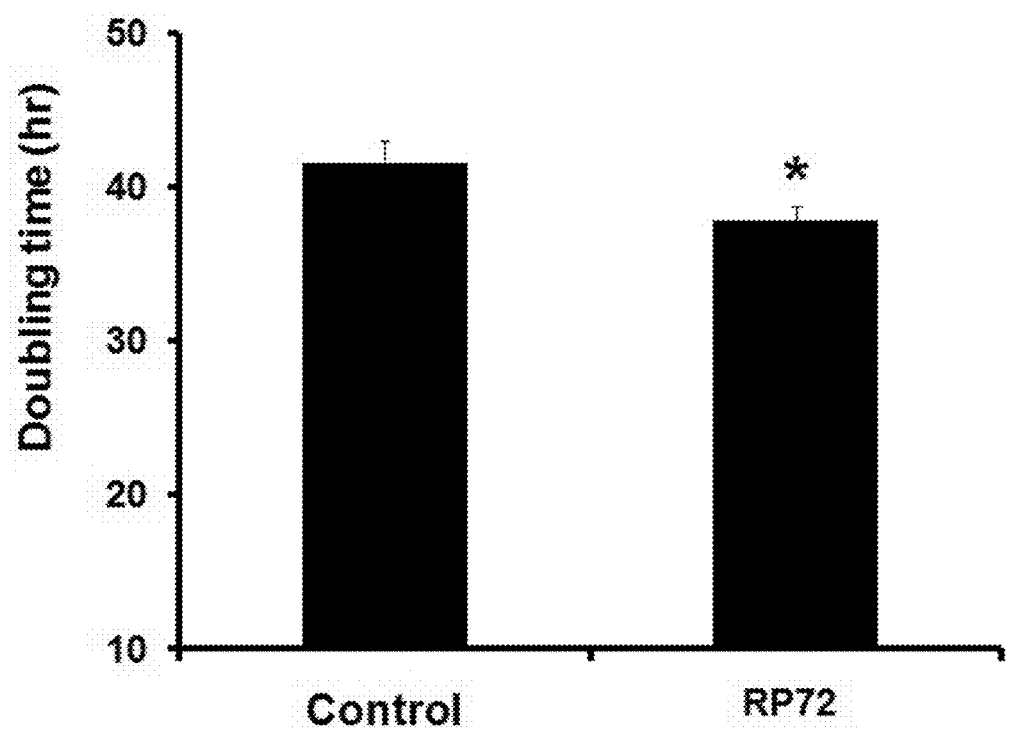
FIG. 2A-FIG. 2B illustrates that RP72 shows anti-growth efficacy in suspended condition of CL1-5 lung cancer cells.
Figure 2B:
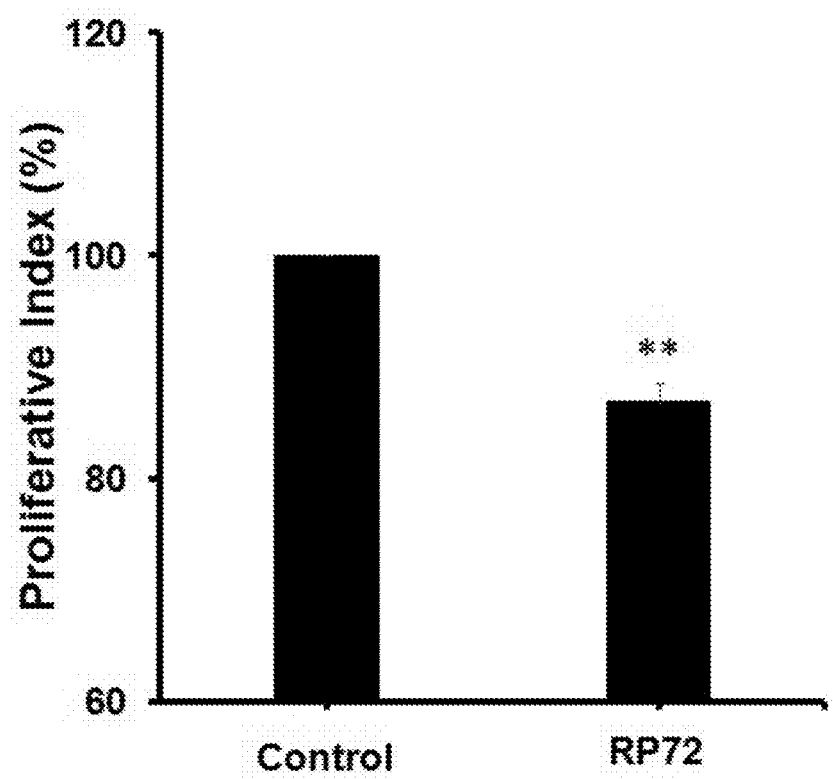

The Novel Modified Chemokine Peptide RP72 Attenuate Growth Efficiency of Tumor Cells The cells can grow in suspended condition means it has self-renew ability and may trigger cancer cells for gaining motility, invasiveness, and metastatic ability. Please refer to FIG. 2A and FIG. 2B, CL1-5 cells were seeded in non-coating 24 well plates with 5×10$^4$ cells/ml and treating/non-treating RP72 (200 ng/ml) at 1$^{st}$ day, then cells were counted and recorded for another 2 days in a row to analyze doubling time of CL1-5 (FIG. 2A) or cells were analyzed by CCK8 reagent after 24 hr seeding and treatment for proliferation rate (FIG. 2B). Analyzing doubling time (FIG. 2A) and proliferation rate (FIG. 2B) by seeding cells in suspended condition, RP72 significantly reduced the anchorage-independent growth, compared to control. Data are shown as mean±SD. *P<0.05; **P<0.01, student's t-test.

Figure 3A:
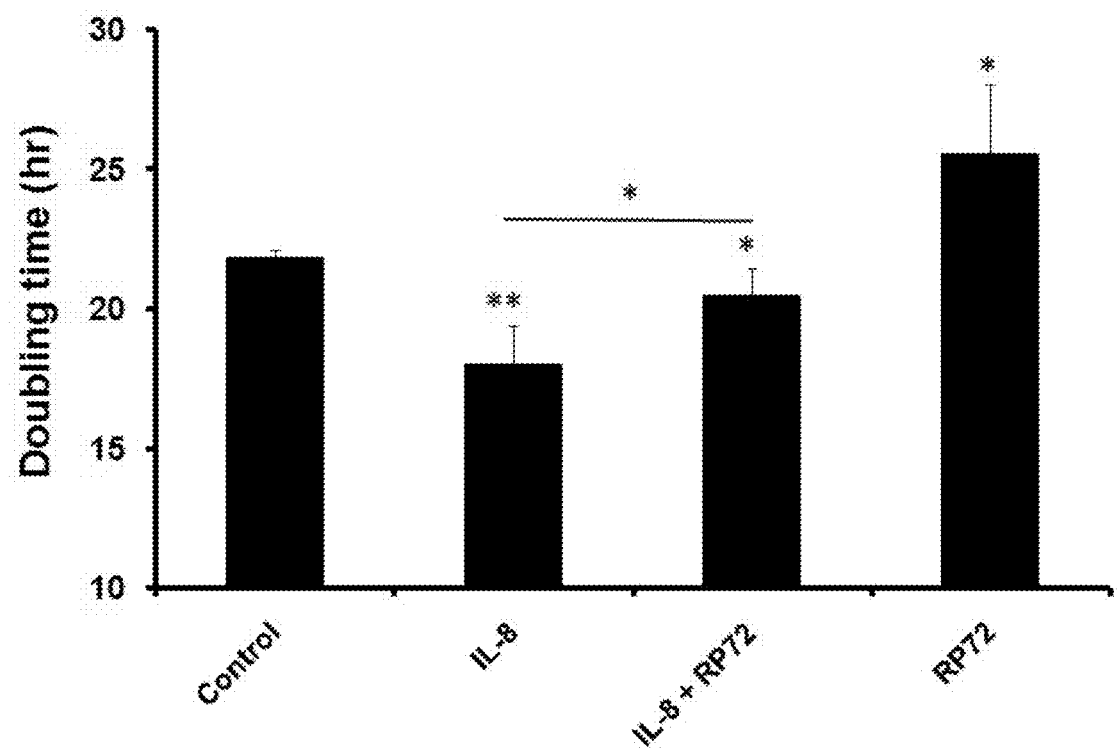
FIG. 3A-FIG. 3B illustrates that that RP72 can slow down the growth rate of LL/2 Lewis lung carcinoma cells.
Figure 3B:
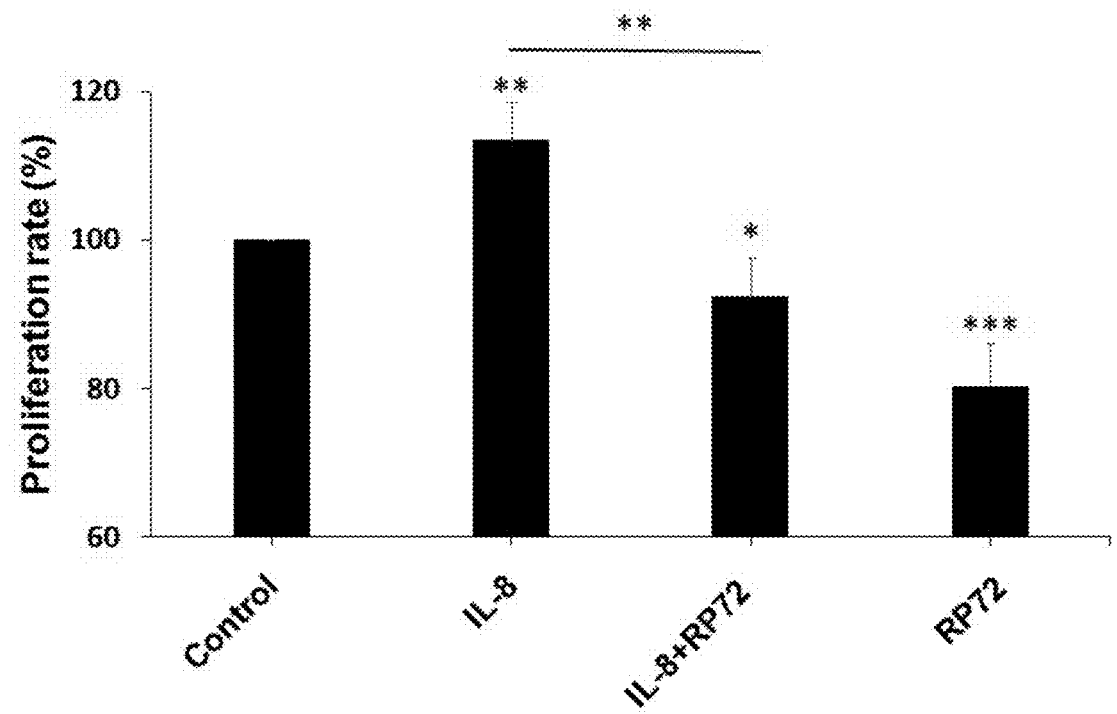

The present invention also illustrate that IL-8 reduced the doubling time of LL/2 and the addition of RP72 with IL-8 was found to increase the doubling-time (FIG. 3A). This result indicates that RP72 can slow down the anoikis-resistant growth rate of cancer cells, as the result in CL1-5. Further, the LL/2 cells were implemented to be suspended growth by CCK8 assay in 24 hr. The results showed that IL-8 indeed significantly increased the anchorage-independent rate in a short period, but when RP72 was present, the growth rate all notably decreased (FIG. 3B). The bars of FIG. 3A and FIG. 3B represent means±SD. *P<0.05; P<0.01; *P<0.001, student's t-test.

Figure 4:
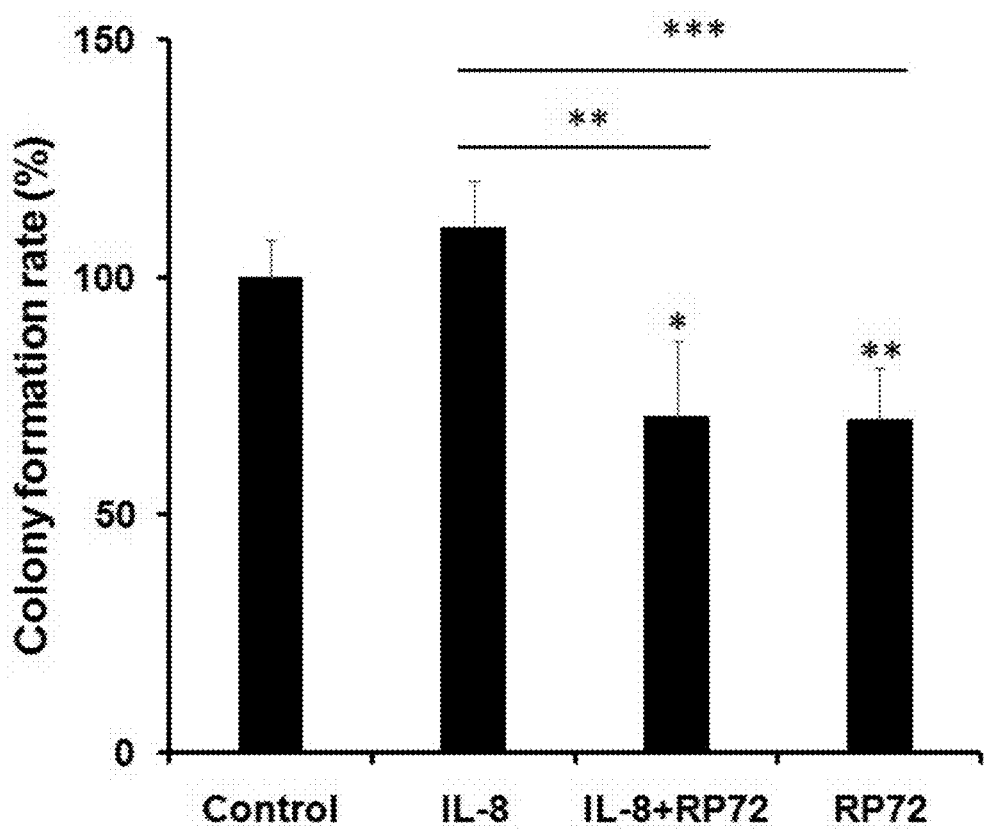
FIG. 4 illustrates that RP72 can inhibit colony formation in BxPC-3 cells.

Moreover, a colony formation assay was performed to evaluate cell proliferation. The BxPC-3 cells treating/non-treating IL-8 (200 ng/ml) or/and RP72 (400 ng/ml). The present invention also showed that RP72 can inhibit colony formation in BxPC-3 (FIG. 4). Statistical significance: *P<0.05, P<0.01, *P<0.001. Thus, the novel modified chemokine peptide RP72 of the present invention can attenuate growth efficiency of tumor cells/cancer cells.

Example 4

Invasion Assay for Tumor Cells

Figure 5A:
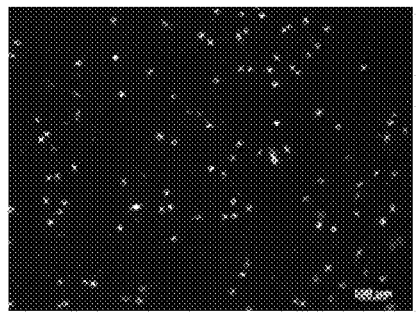
FIG. 5A-FIG. 5E illustrates that IL-8-induced CL1-5 NSCLC cells invasion rates are inhibited by RP72.
Figure 5B:
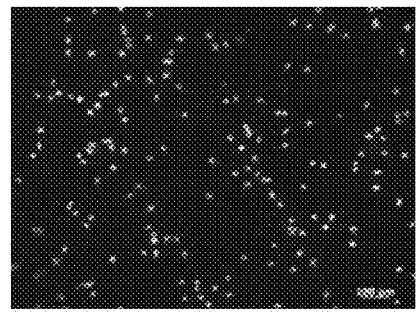
Figure 5C:
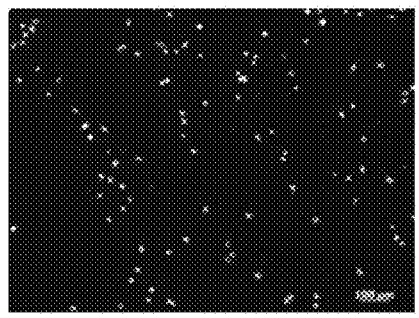
Figure 5D:
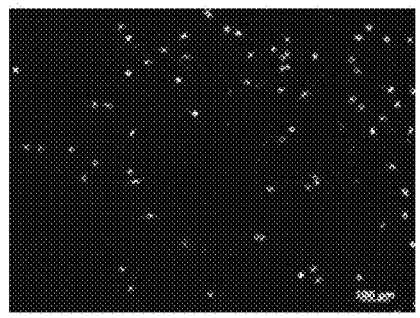
Figure 5E:
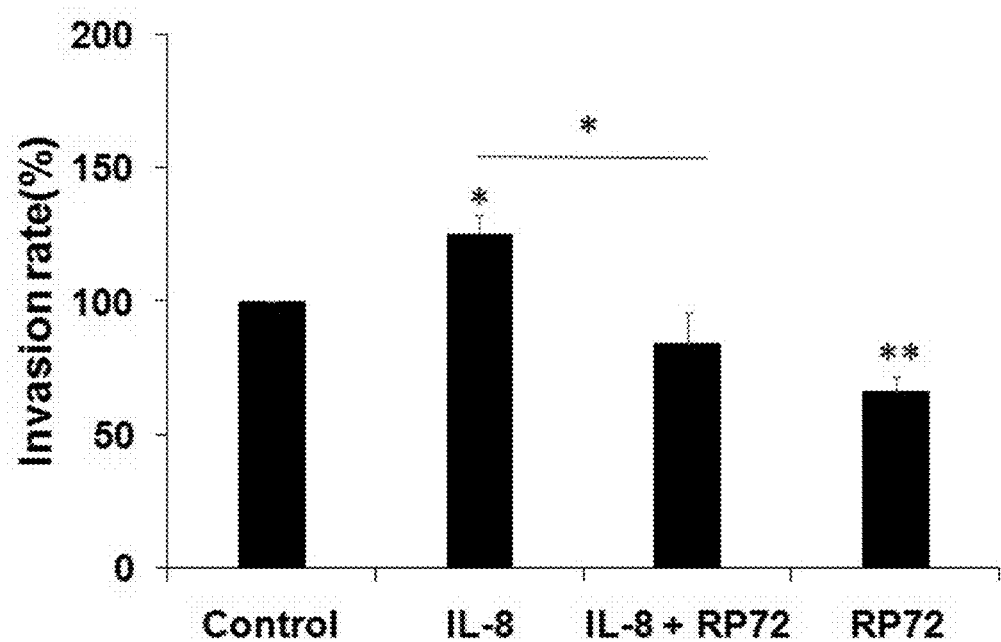

Please refer to FIG. 5A-FIG. 5E, CL1-5 cells were seeded onto Matrigel-coated polycarbonate filters with 2.5×10$^4$ cells treated with RP72 (200 ng/ml) with/without IL-8 (100 ng/ml). (FIG. 5A represented control group. FIG. 5B represented the cells treated with IL-8. FIG. 5C represented the cells treated with IL-8 and RP72. FIG. 5D represented the cells treated with RP72.) The cells were then incubated for 24 hr and were analyzed by staining PI and counted under a microscope. Representative fields of invasive cells on the transwell membrane (at 100× magnification) and the invasion rate are shown in FIG. 5A-FIG. 5E and the bar chart. Results were obtained from five random fields in each well and were repeated three times. The bars of FIG. 5E represent means±SD. *P<0.05; ***P<0.001, student's t-test. The outcome shows IL-8 induce the cell invasion and RP72 can inhibit the invasion, compared to control or IL-8 groups (FIG. 5A-FIG. 5E). Taken together, IL-8 secretion can trigger tumor cells/cancer cells invasion simultaneously and RP72 can attenuate IL-8-induced invasion.

Figure 6A:
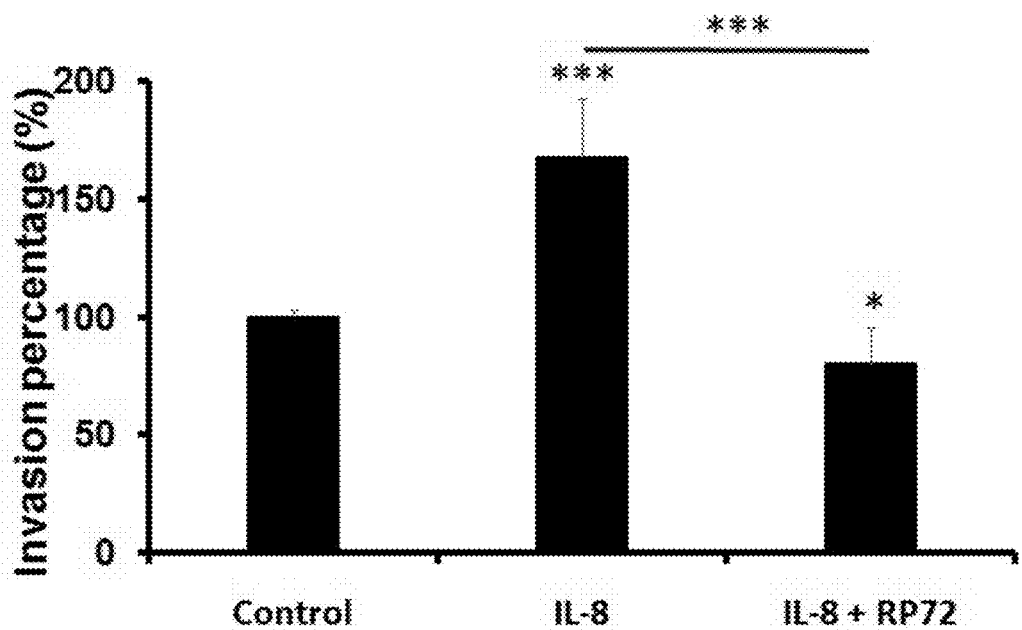
FIG. 6A-FIG. 6B are illustrated that IL-8/MIP-2-induced invasion rates are inhibited by RP72.
Figure 6B:
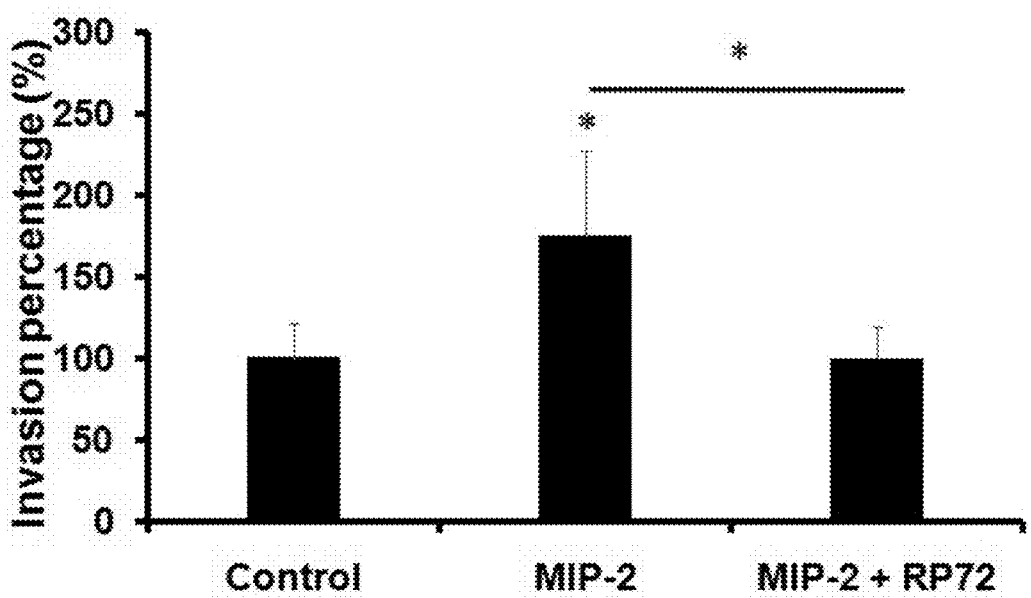

Additionally, the LL/2 cells were seeded onto Matrigel-coated polycarbonate filters to analyze their invasive potentials. The cells were then incubated for 24 hr in chambers and were analyzed by staining PI and counted under a microscope. Representative fields of invasive cells on the transwell membrane (at 100× magnification) and the invasion rate were shown. The LL/2 cells treated with IL-8 (100 ng/ml) or IL-8+RP72 (200 ng/ml) were shown in FIG. 6A. The results showed that IL-8 excited LL/2's invasion ability. However, RP72 significantly suppressed IL-8 stimulated cell invasion. On the other hand, the LL/2 cells were also treated with 50 ng/ml MIP-2 (the functional homologue of IL-8 in murine) or MIP-2+RP72 (200 ng/ml) (FIG. 6B). RP72 also decreased the invasion rate in the MIP-2 stimulated group. These results suggested that not only RP72 can attenuate IL-8-induced invasion but also attenuate the MIP-2-induced invasion in murine. The bars of FIG. 6A and FIG. 6B represent means±SD. *P<0.05; ***P<0.001, student's t-test.

Figure 7:
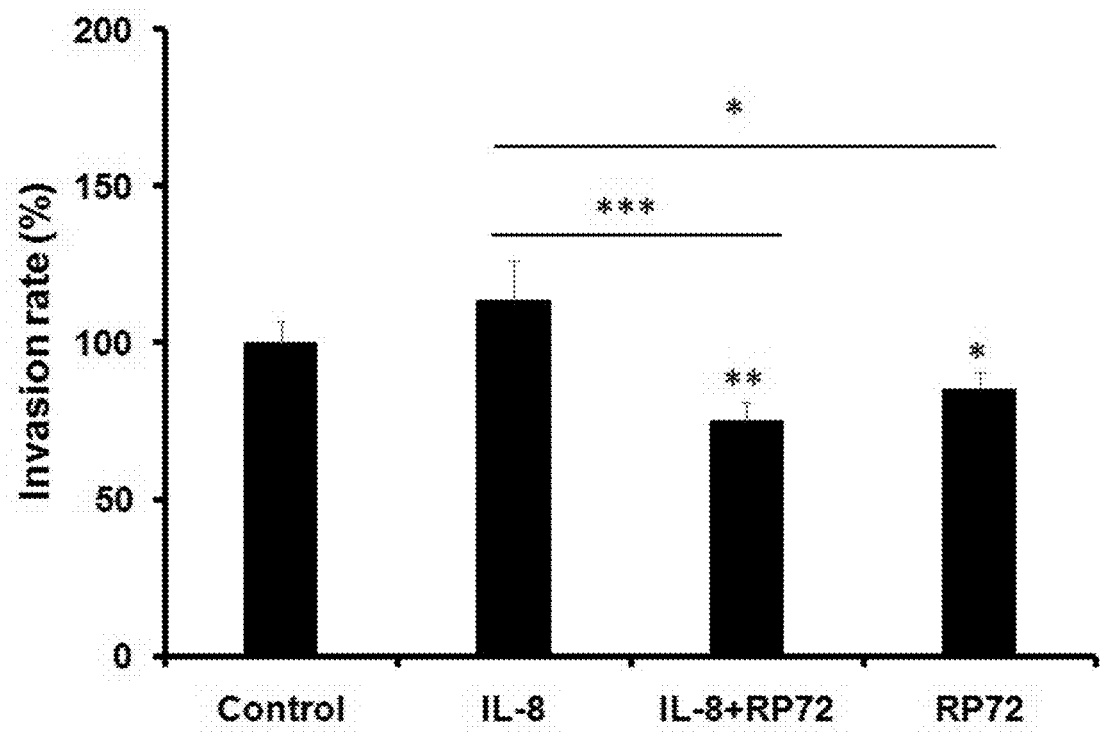
FIG. 7 illustrates that RP72 can inhibit cell invasion in BxPC-3.

Moreover, the BxPC-3 cells treated with IL-8 (200 ng/ml) or/and RP72 (400 ng/ml) were shown in FIG. 7. The present invention exhibit that CXCL8 can enhance the cell invasion. However, RP72 can neutralize the effect of CXCL8 to reduce the invasive rate in BxPC-3.

Example 5

RP72 can Protect and Recover the Loosed Endothelial Cell-Junction Induced by IL-8

IL-8 (100 ng/ml) and CL1-5 condition medium made cell-junction loosed by showing much lower Rb of impedance than treating with RP4 (200 ng/ml).*P<0.05; P<0.01; *P<0.001, student's t-test.

Endothelial frequency resistance (impedance) was modeled for the calculation of cell-cell adhesion (Rb) and cell-matrix interaction (Alpha) via Electric Cell-Substrate Impedance Sensing (ECIS) monitoring in real time. HUVEC cells were seeded 400 μl of $5 \times 10^4$ cells/ml into each well of prepared arrays at $1^{st}$ day, after 24 hr attachment and ECIS-balance, treatment were added into wells. The above-mentioned treatment include IL-8 (100 ng/ml), IL-8 combined with RP72, RP72 (200 ng/ml), CL1-5 condition medium (CM), IL-8 knock down CL1-5 CM, and CL1-5 CM combined with RP72.

Figure 8A:
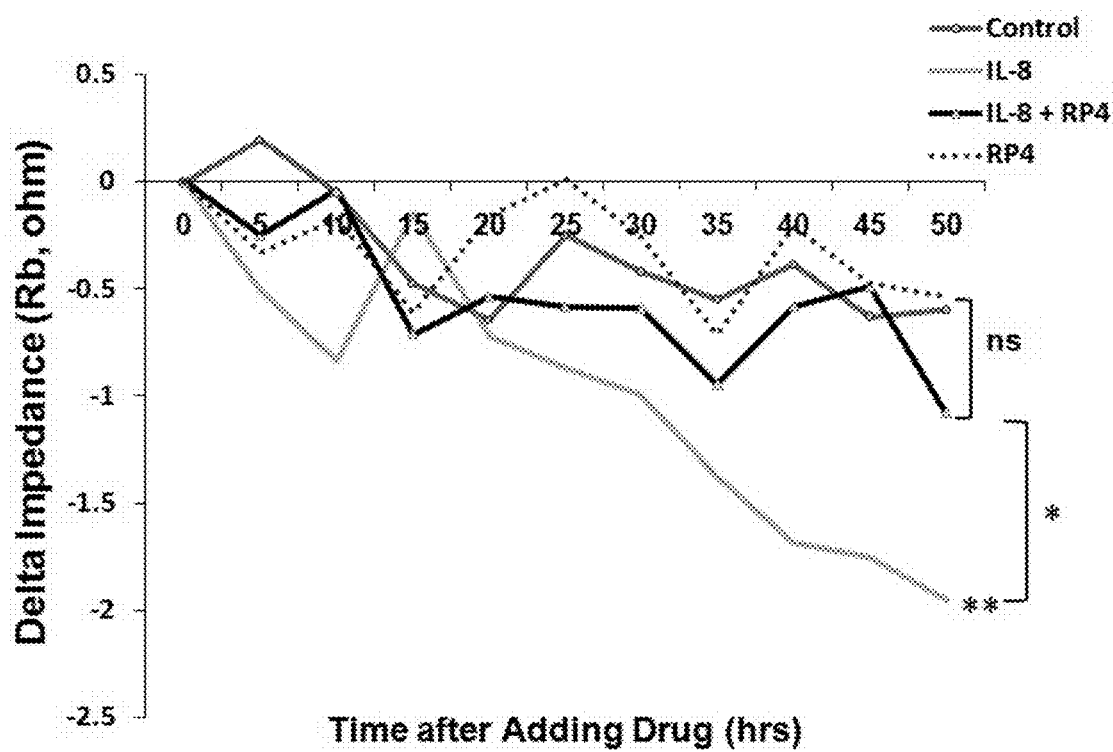
FIG. 8A-FIG. 8B illustrates that RP72 can protect and recover the loosed endothelial cell-junction induced by IL-8.
Figure 8B:
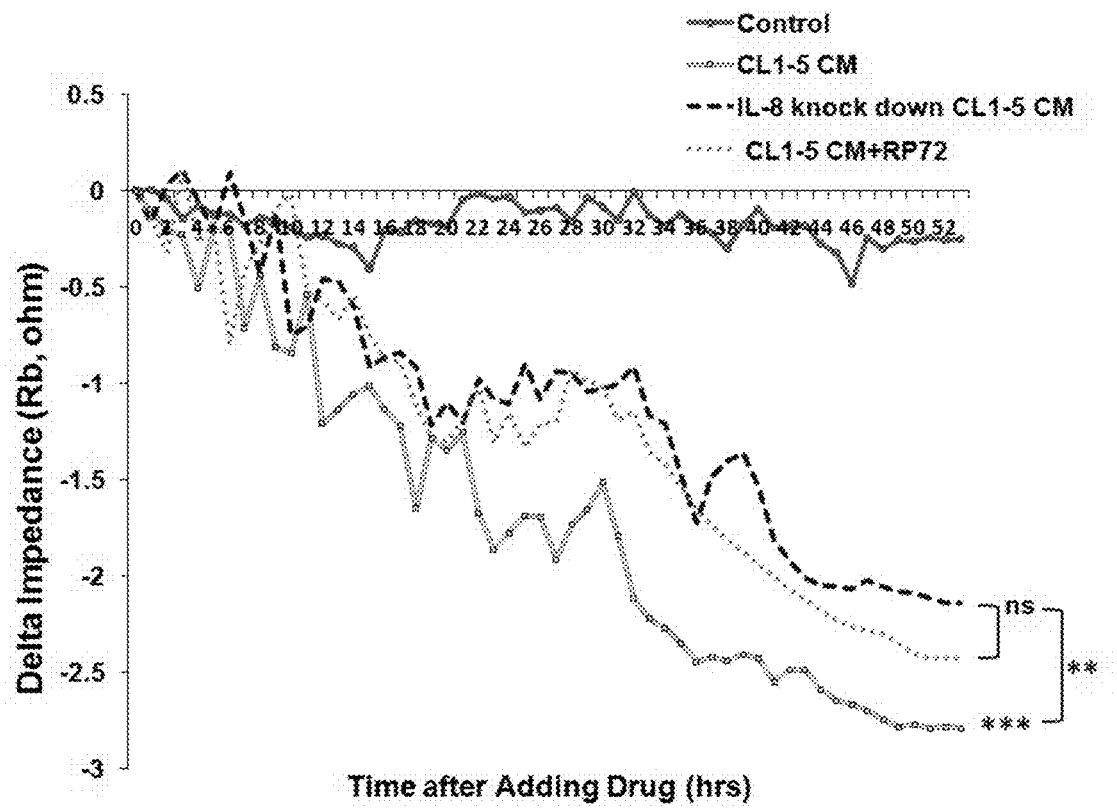

Here the present invention use generally AC source with a 4000-Hz to collect impedance −Rb (ohm), the time-dependent difference of Rb was calculated and the results find out that IL-8 indeed trigger loosed cell junction between HUVEC by decrease value of Rb. However, RP72 treatment can recover this situation (FIG. 8A). Besides, treating CL1-5 condition medium (CM) with HUVEC shows the same trend. Nonetheless, IL-8 knock down CL1-5 CM significantly attenuates loosed cell junction by lower the value of delta impedance (Rb, ohm), and the result non-significantly differ from CL1-5 CM+RP72 (FIG. 8B). In other words, IL-8 (100 ng/ml) and CL1-5 condition medium made cell-junction loosed by showing much lower Rb of impedance than treating with RP4 (200 ng/ml).*P<0.05; P<0.01; *P<0.001, student's t-test. In brief, these ECIS results of the present invention demonstrate that IL-8 secreted from tumor cells/cancer cells promotes cell junction of endothelial cells disrupted and trigger tumor cells/cancer cells for gaining motility, invasiveness, and metastatic ability.

Example 6

RP72 Inhibits Tumor Growth and Prolongs the Survival Rate

LL/2 cells were subcutaneously inoculated to male C57BL/6 mice (4 to 6-weeks) as the LL/2 allogeneic model. Then, RP72 (500 μg/kg) or saline (control group) was administrated by i.p. injection every 3 times a week. The tumor size were recorded while mice were scarified. The survival rates of tumor-bearing mice were observed and recorded continuously until all mice were scarified. Data are shown as mean±SEM (n=6). *P<0.05; ***P<0.001 compared with control group, student's t-test.

Figure 9A:
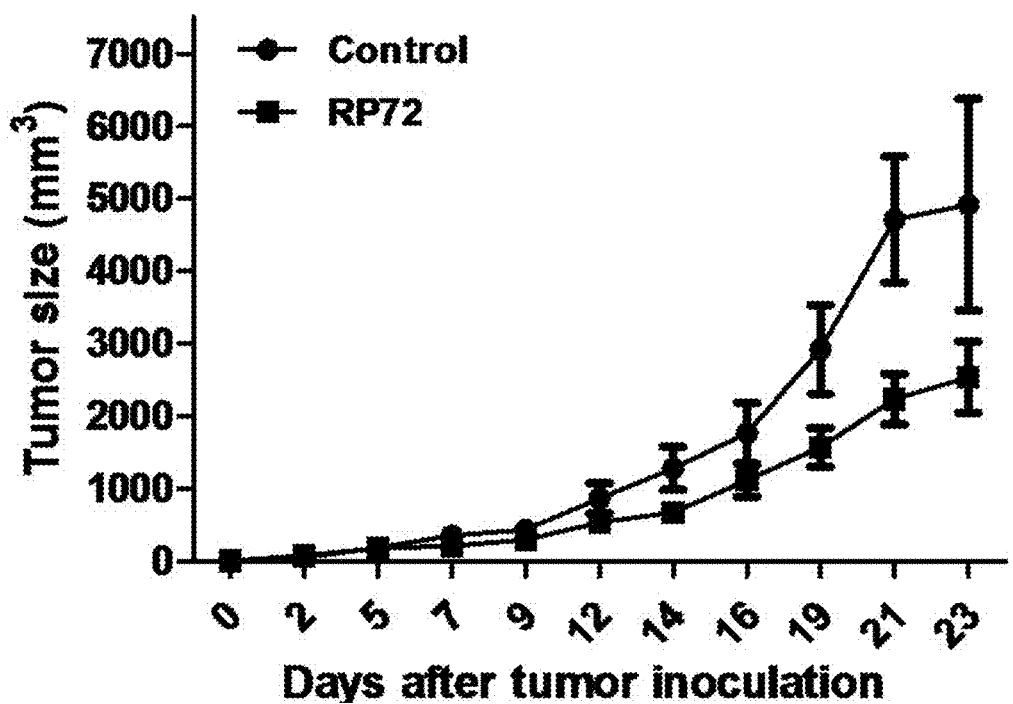
FIG. 9A-FIG. 9B illustrates one embodiment that RP72 inhibits tumor growth and prolongs the survival rate.
Figure 9B:
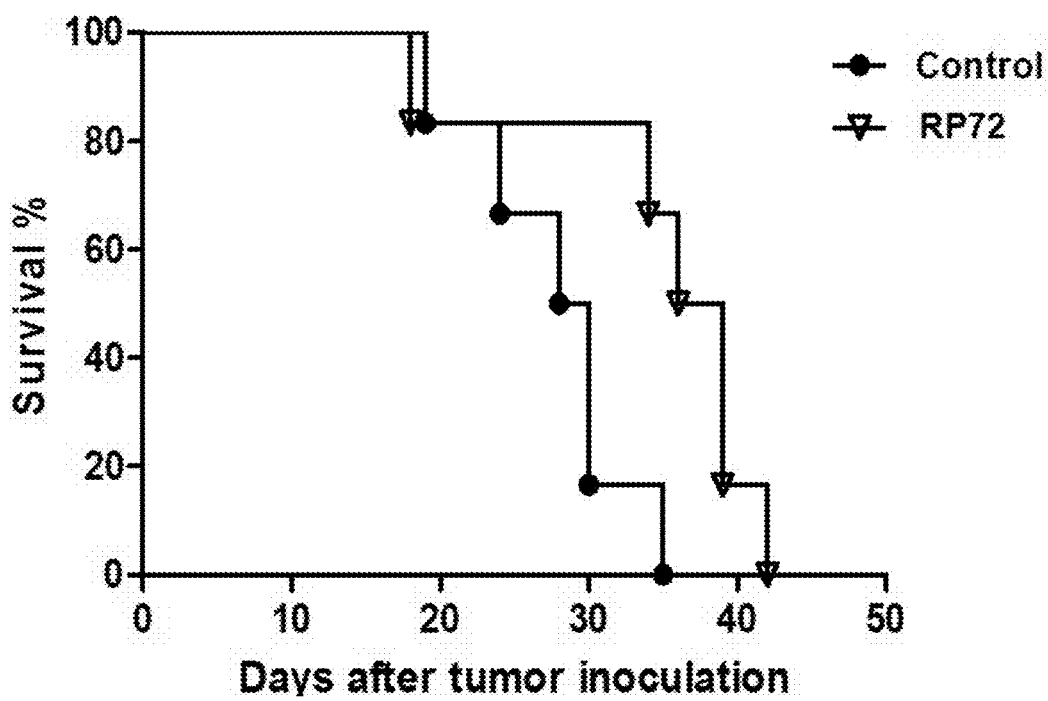

RP72 significantly inhibited tumor growth in vivo compared to the saline control group (FIG. 9A). Additionally, treatment of RP72 did not lead to a reduction in the body weight of mice, meaning that RP4 might have no toxicity effect in vivo. Furthermore, RP72 prolonged the lifespan of tumor-bearing mice (FIG. 9B). The median lethal time (LT50) of RP72 group and control group were 36 days and 28 days, respectively. These results demonstrated that RP72 could significantly suppress tumor growth and improve the survival rate of C57BL/6 mice.

Example 7

Figure 10:
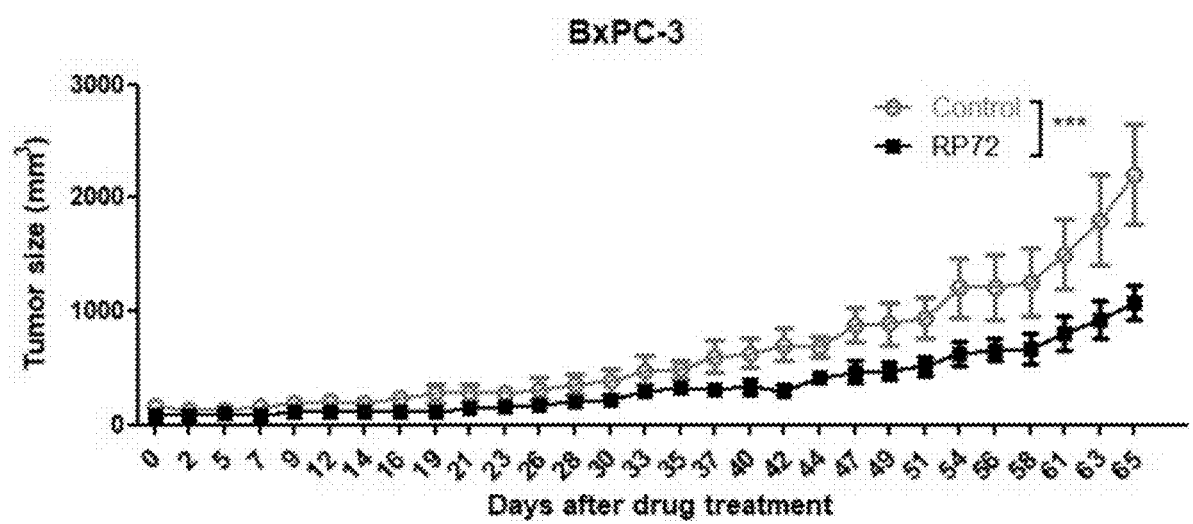
FIG. 10 illustrates another embodiment that RP72 can reduce tumor size via administrating a subject.

Xenograft Study of RP72 in Treating Animals with Pancreatic Cancer 4-week old male BALB/c nude mice were inoculated BxPC-3 cells subcutaneously as the BxPC-3 model. After 7 days, mice were treated with saline or RP72 (500 μg/kg) by i.p injection three times a week. The initiation tumor size was 128.5±47.8 $mm^3$ in first treatment. It was found that RP72 significantly inhibited the tumor growth in vivo (FIG. 10). Additionally, treatment of RP72 didn't lead to reduce the body weight of mice (data not shown), meaning that RP72 might have no toxicity effect in vivo. These results demonstrated that RP72 could significantly suppress the tumor growth and improve the survival rate of BALB/c nude mice.

As mentioned above, the modified chemokine of the present invention can effectively inhibit tumor growth and angiogenesis and treat cancer.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes, and substitutions are intended in the foregoing disclosures. It will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

What is claimed is:

1. A modified chemokine peptide, wherein the modified chemokine peptide is RP72 set forth in SEQ ID NO: 1.

2. A pharmaceutical composition for treating a lung cancer or a pancreatic cancer, comprising a therapeutically effective amount of the modified chemokine peptide RP72 set forth in SEQ ID NO: 1 and a pharmaceutically acceptable excipient.

3. A method for treating a lung cancer or a pancreatic cancer in a subject, wherein the method comprises administering to said subject an effective amount of the modified chemokine peptide RP72 set forth in SEQ ID NO: 1 and a pharmaceutically acceptable excipient.

4. A kit comprising the modified chemokine peptide RP72 set forth in SEQ ID NO: 1 of claim 1.

* * * * *

SEQUENCE LISTING

```
<160> NUMBER OF SEQ ID NOS: 7

<210> SEQ ID NO 1
<211> LENGTH: 72
<212> TYPE: PRT
<213> ORGANISM: Artificial Sequence
<220> FEATURE:
<223> OTHER INFORMATION: RP72 synthesized from the laboratory

<400> SEQUENCE: 1

Gly Ser Lys Glu Leu Arg Cys Gln Cys Ile Arg Ser Tyr Ser Lys Pro
```

```
1               5                   10                  15
Phe His Pro Lys Phe Ile Lys Glu Leu Arg Val Ile Pro Ala Ser Gln
            20                  25                  30

Phe Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser
65                  70
```

```
<210> SEQ ID NO 2
<211> LENGTH: 21
<212> TYPE: DNA
<213> ORGANISM: Artificial Sequence
<220> FEATURE:
<223> OTHER INFORMATION: forward primer for CXCL8

<400> SEQUENCE: 2
gagcactcca taaggcacaa a                                          21

<210> SEQ ID NO 3
<211> LENGTH: 18
<212> TYPE: DNA
<213> ORGANISM: Artificial Sequence
<220> FEATURE:
<223> OTHER INFORMATION: reverse primer for CXCL8

<400> SEQUENCE: 3
atggttcctt ccggtggt                                              18

<210> SEQ ID NO 4
<211> LENGTH: 20
<212> TYPE: DNA
<213> ORGANISM: Artificial Sequence
<220> FEATURE:
<223> OTHER INFORMATION: forward primer for CXCR1

<400> SEQUENCE: 4
gaccaacatc gcagacacat                                            20

<210> SEQ ID NO 5
<211> LENGTH: 20
<212> TYPE: DNA
<213> ORGANISM: Artificial Sequence
<220> FEATURE:
<223> OTHER INFORMATION: reverse primer for CXCR1

<400> SEQUENCE: 5
tgcttgtctc gttccacttg                                            20

<210> SEQ ID NO 6
<211> LENGTH: 25
<212> TYPE: DNA
<213> ORGANISM: Artificial Sequence
<220> FEATURE:
<223> OTHER INFORMATION: forward primer for CXCR2

<400> SEQUENCE: 6
ggctaagcaa aatgtgatat gtacc                                      25

<210> SEQ ID NO 7
<211> LENGTH: 20
<212> TYPE: DNA
<213> ORGANISM: Artificial Sequence
```

```
<220> FEATURE:
<223> OTHER INFORMATION: reverse primer for CXCR2

<400> SEQUENCE: 7
caaggttcgt ccgtgttgta                                                   20
```